US00PP13453P3

(12) United States Plant Patent

Olesen et al.

(10) Patent No.: US PP13,453 P3
(45) Date of Patent: Jan. 7, 2003

(54) MINIATURE ROSE PLANT NAMED 'POULGO001'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 22 days.

(21) Appl. No.: 09/776,560

(22) Filed: Feb. 1, 2001

(65) Prior Publication Data

US 2002/0152509 P1 Oct. 17, 2002

(51) Int. Cl.[7] ..... A01H 5/00
(52) U.S. Cl. ..... Plt./117
(58) Field of Search ..... Plt./117, 116, 124

*Primary Examiner*—Bruce R. Campell
*Assistant Examiner*—June Hwu

(57) ABSTRACT

A new miniature rose which has abundant, white flowers and attractive foliage. This new and distinct variety has shown to be uniform and stable in the resulting generations from asexual propagation.

1 Drawing Sheet

SUMMARY OF THE INVENTION

Classification

*Botanical.*—*Rosa hybrida* 'POULgo001'.

*Commercial.*—Miniature.

The present invention constitutes a new and distinct variety of miniature rose plant which originated from a controlled crossing between an unnamed and unpatented seedling and 'POULrijk', described and illustrated in U.S. Plant Pat. No. 12,519 issued Apr. 2, 2002. The two parents were crossed during the summer of 1994 and the resulting seeds were planted in a controlled environment in Fredensborg, Denmark. The new variety is named 'POULgo001'.

The new rose may be distinguished from its seed parent, an unnamed seedling, by the following combination of characteristics:

1. The unnamed seed parent exhibits pink blooms, while 'POULgo001' has white blooms.

2. The unnamed seed parent is a miniature rose with an upright habit, whereas 'POULgo001' is a miniature rose with a pendulant habit.

The new variety may be distinguished from its pollen parent, 'POULrijk' by the following combination of characteristics:

1. The pollen parent has pink blooms, while those of 'POULgo001' are white.

2. The pollen parent has smaller flowers than 'POULgo001'.

The objective of the hybridization of this rose variety was to create a new and distinct variety for garden use with unique qualities, such as:

1. Uniform and abundant white flowers;

2. Vigorous, pendulant growth when propagated with cuttings;

3. Disease resistance.

4. A miniature rose suitable for use in hanging basket containers in the nursery industry.

This combination of qualities is not present in previously available commercial cultivars of this type and distinguish 'POULgo001' from all other varieties of which we are aware.

As part of their rose development program, L. Pernille Olesen and Mogens N. Olesen germinated the seeds from the aforementioned hybridization during winter of 1994 and conducted evaluations on the resulting seedlings in a controlled environment in Fredensborg, Denmark. 'POULgo001' was selected in the spring of 1995 by the inventors as a single plant from the progeny of the aforementioned hybridization.

Asexual reproduction of 'POULgo001' by traditional budding and rooted cuttings was first done by L. Pernille and Mogens N. Olesen in their nursery in Fredensborg, Denmark in July 1995. This initial and other subsequent asexual propagations conducted in controlled environments have demonstrated that the characteristics of 'POULgo001' are true to type and are transmitted from one generation to the next.

BRIEF DESCRIPTION OF THE DRAWING

The accompanying color illustration shows as true as is reasonably possible to obtain in color photographs of this type the variety rose 'POULgo001'. Specifically illustrated in SHEET 1 is a plant of 'POULgo001' growing in a 20-cm hanging basket.

DETAILED DESCRIPTION OF THE VARIETY

The following is a description of 'POULgo001', as observed in its growth in Jackson County, Oreg., on plants aged 18 weeks. Color references are made using The Royal Horticultural Society (London, England) Colour Chart, 1995, except where common terms of color are used. For a comparison, several physical characteristics of the rose variety 'POULterp', a rose variety from the same inventors described and illustrated in U.S. Plant Pat. No. 12,623 issued May 14, 2002 are compared to 'POULgo001' in Chart 1.

CHART 1

| | 'POULgo001' | 'POULterp' |
|---|---|---|
| Color of open flower, outer side, middle zone. | White Group 155C | White Group 155B-C |
| Flower diameter | 50–80 mm | 35 mm |

CHART 1-continued

| | 'POULgo001' | 'POULterp' |
|---|---|---|
| Plant growth | 40 to 60 cm (h) × 60 cm (w) | 45–60 cm (h) × 120–150 cm (w) |

Parents:
*Seed parent*.—Unnamed seedling.
*Pollen parent*.—'POULrijk'.

FLOWER AND FLOWER BUD

Blooming habit: Continuous.
Flower bud:
*Size*.—15 mm in length from base of receptacle to end of bud.
*Bud form*.—Pointed ovoid.
*Bud color*.—As sepals unfold, White Group 155C; White Group 155C at ¼ opening.
*Sepals*.—Shape: Sepal apex is cirrose; base is flat at union with peduncle. Length: 15 mm. Width: 5 mm. Color: Upper surface is Yellow-Green Group 144 A at margins and Yellow-Green Group 144 B and C. Lower surface is Yellow-Green Group 144 B and C. Appendages: Weak foliaceous appendages on 4 of the five sepals. Pubescence: Moderate. Stipitate Glands: Stipitate glands present on sepal margins.
*Receptacle*.—Surface: Glaucous. Shape: Funnel-shaped. Size: 5 mm (h)×6 mm (w). Color: Green Group 144B, with some anthocyanin intonation of Greyed-Purple Group 183D.
*Peduncle*.—Surface: Many stipitate glands and fine white hairs present. Length: 28 to 32 mm. Color: Yellow-Green Group 144B. Strength: Somewhat strong. Anthocyanin: Greyed-Purple Group 183D.
*Borne*.—2 to 3 buds per stem.
Flower bloom:
*Fragrance*.—Weak.
*Size*.—Average flower diameter is 50–80 mm when open.
*Form*.—Shape of flower when viewed from the side: Upper part: Flat. Lower part: Flattened convex. Viewed from above: Irregularly rounded.
*Petalage*.—Very double. Average range: 60 to 65 petals under normal conditions.
*Duration*.—7 to 10 days.
Color:
*Petals*.—Inner Side: Middle zone: White Group 155C. Marginal zone: White Group 155C. Basal petal spot: No coloration observed. Outer side: Middle zone: White Group 155C. Marginal zone: White Group 155C. Basal petal spot: No coloration observed.
*General tonality*.—On open flower White Group 155C.
Petals:
*Petal reflex*.—Weak.
*Undulation of margin*.—Weak.
*Size*.—8 mm wide and 10 mm long.
*Shape*.—Obovate.
*Margin type*.—Entire.
*Apex shape*.—Rounded and cuspidate.
*Petaloids*.—Quantity: 4 to 6. Size: 4 mm wide and 6 mm long. Shape: Ovate. Color: White Group 155C. Texture: Smooth.
Reproductive organs:
*Filaments*.—None observed.
*Pistils*.—Length: 4 mm. Quantity: 45.
*Pollen*.—None observed.
*Anthers*.—None observed.
*Stigmas*.—Color: Yellow-Green Group 144D.
*Styles*.—Color: Yellow-Green Group 150D.
*Hips*.—None observed; the plant is sterile.
Seed production: No seeds produced.

PLANT

Plant growth: Spreading. Procumbent to arching habit. Height 40–60 cm.
Stems:
*Old wood*.—Texture: Smooth. Color: Yellow-Green Group 144A.
*Young wood*.—Texture: Smooth. Color: Yellow-Green Group 144B.
*Thorns*.—Incidence: 4 to 5 thorns per 10 cm of stem. Size: 2 to 3 mm long. Shape: Concave. Color: Greyed-Orange Group 167B.
Plant foliage:
*Number of leaflets on normal leaves in middle of a stem*.—5.
*Leaf size*.—65 mm (l) by 35 mm (w).
*Quantity*.—Average.
*Color*.—Mature foliage: Upper Leaflet Surface: Green Group 137A. Lower Leaflet Surface: Green Group 138B. Juvenile foliage: Upper Leaflet Surface: Green Group 137A. Lower Leaflet Surface: Green Group 138B. Anthocyanin intonation: None noted.
Plant leaflets:
*Stipule*.—Length: 11 mm. Color: Yellow-Green Group 144B. Anthocyanin: Greyed-Red Group 178A. Margins: Some stipitate glands present.
*Petiole*.—Length: 8–11 mm. Color: Green Group 137A. Underneath: Green Group 137B. Stipitate glands and occasionally a single, small thorn. Margins: Stipitate glands present. Anthocyanin: None observed.
*Rachis*.—Length: 15 mm. Color: Green Group 144A. Underneath: Green Group 144A. Stipitate glands and occasionally a single, small thorn. Margins: Stipitate glands present. Anthocyanin: None observed.
*Leaflet*.—Edge: Serrated. Shape: Ovate. Surface: Moderately glossy. Texture: Thin. Arrangement: Odd pinnate. Venation: Reticulate.
Disease resistance: Above average resistance to mildew, rust, black spot, and Botrytis under normal growing conditions in Jackson County, Oreg.
Cold hardiness: The variety 'POULgo001' has been found to be resistant to damage from cold in USDA Zone 7.

We claim:

1. A new and distinct variety of rose plant of the miniature rose class, substantially as herein illustrated and described as a distinct and novel rose variety due to its abundant white flowers, procumbent to arching habit, disease resistance, and extended period of bloom.

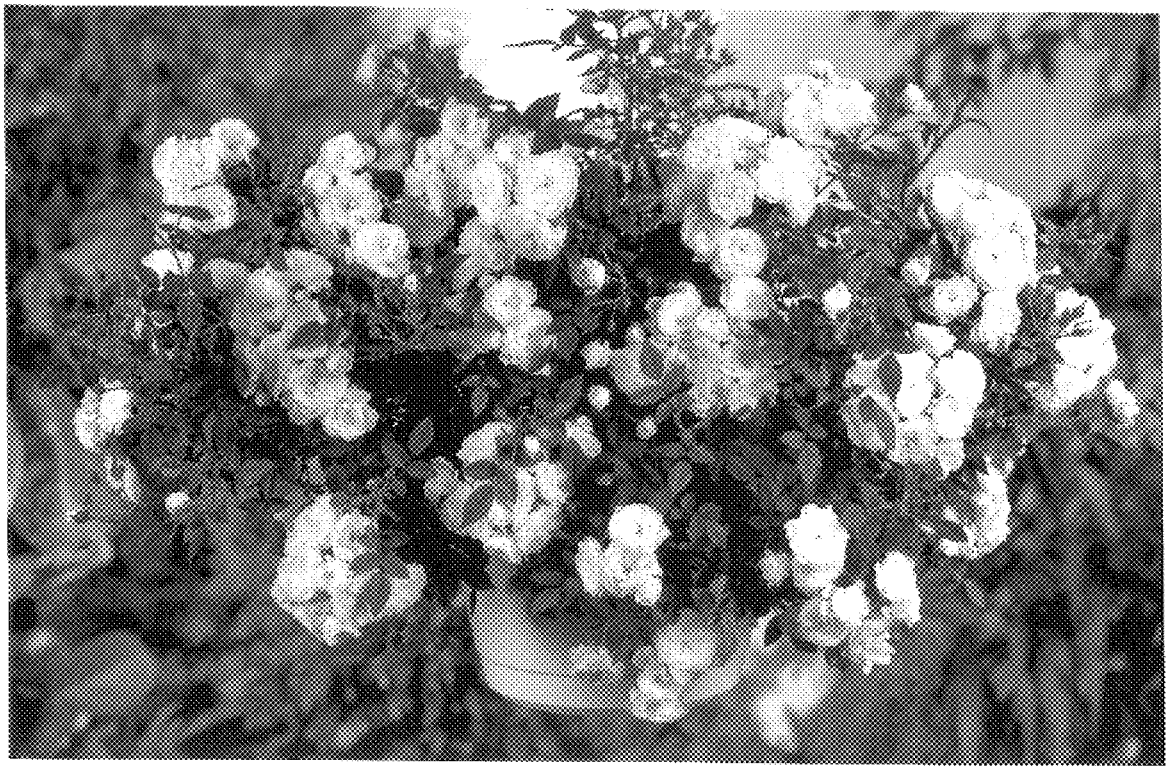

* * * * *